(12) United States Patent
Mollus et al.

(10) Patent No.: US 8,000,445 B2
(45) Date of Patent: Aug. 16, 2011

(54) ROTATIONAL X-RAY SCAN PLANNING SYSTEM

(75) Inventors: Sabine Mollus, Aachen (DE); Juergen Weese, Aachen (DE); Jens Wiegert, Aachen (DE); Robert Johannes Frederik Homan, Batenburg (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 249 days.

(21) Appl. No.: 12/375,573

(22) PCT Filed: Jul. 18, 2007

(86) PCT No.: PCT/IB2007/052854
§ 371 (c)(1),
(2), (4) Date: Jan. 29, 2009

(87) PCT Pub. No.: WO2008/015611
PCT Pub. Date: Feb. 7, 2008

(65) Prior Publication Data
US 2009/0262886 A1    Oct. 22, 2009

(30) Foreign Application Priority Data
Jul. 31, 2006    (EP) .................................... 06118152

(51) Int. Cl.
*H05G 1/64* (2006.01)

(52) U.S. Cl. .............................. 378/98; 378/4; 378/901
(58) Field of Classification Search .................. 378/4, 8, 378/20, 91, 98, 98.2, 901
See application file for complete search history.

(56) References Cited

U.S. PATENT DOCUMENTS

| | | | |
|---|---|---|---|
| 5,457,724 A | 10/1995 | Toth | |
| 6,049,582 A | 4/2000 | Navab | |
| 7,478,949 B2 * | 1/2009 | Niessen et al. | 378/205 |
| 2003/0097062 A1 | 5/2003 | Toth et al. | |
| 2005/0089139 A1 | 4/2005 | Sukovic | |
| 2005/0148850 A1 | 7/2005 | Lahm et al. | |

FOREIGN PATENT DOCUMENTS

| | | |
|---|---|---|
| WO | 2004080309 A2 | 9/2004 |
| WO | 2005009243 A1 | 2/2005 |
| WO | 2005041775 A1 | 5/2005 |
| WO | 2005092196 A1 | 10/2005 |
| WO | 2007126932 A1 | 11/2007 |

* cited by examiner

*Primary Examiner* — Jurie Yun

(57) ABSTRACT

In three-dimensional X-ray imaging, with C-arm systems, scan setup has to be performed manually under fluoroscopic control. According to an exemplary embodiment of the present invention, a scan planning system for planning a data acquisition process is provided, which is adapted to predict a field of view to be reconstructed and an image quality in the field of view with respect to the actual three-dimensional scan parameter set and previously acquired images or other information. The scan planning system may be accomplished by a stand control unit.

19 Claims, 2 Drawing Sheets

ROTATIONAL X-RAY SCAN PLANNING SYSTEM

The invention relates to the field of X-ray imaging. In particular, the invention relates to a scan planning system for planning a data acquisition process of an object of interest with a rotational X-ray C-arm examination apparatus, to a rotational X-ray C-arm examination apparatus, to a method of planning a data acquisition process, to an image processing device, to a computer-readable medium and to a program element.

Scan planning techniques are known in the field of diagnostic imaging. In computed tomography (CT) and magnetic resonance imaging (MR) prior to diagnostic imaging a so-called scout scan is performed. A scout scan is typically obtained from a fixed angular position (lateral and/or anterior-posterior view) and features low spatial resolution. The scout images are primarily used to give an anatomical survey, to localise body structures and to organize the slice locations for following acquisitions.

Scan planning (scan setup) in rotational X-ray imaging has to be performed manually under fluoroscopic control. This process may be tedious and error prone, since often contradicting clinical and technical requirements have to be considered.

It would be desirable to have an improved three-dimensional scan setup.

It should be noted that the following described exemplary embodiments of the invention apply also to the method of planning a data acquisition process of an object of interest with a rotational X-ray C-arm examination apparatus, to the computer-readable medium, to the image processing device, to the examination apparatus and the program element.

According to an exemplary embodiment of the present invention, a scan planning system for planning a data acquisition process of an object of interest with a rotational X-ray C-arm examination apparatus is provided. The scan planning system comprises a control unit for predicting a field of view to be reconstructed and the image quality in the field of view on the basis of at least one of a scan parameter set and a previously acquired reference data set.

This may simplify three-dimensional imaging in a cathlab and provide for a prediction of the scan quality beforehand. Therefore, according to this exemplary embodiment of the invention, the quality of the scan may no longer depend on the expertise of the user.

According to another exemplary embodiment of the present invention, the reference data set is a three-dimensional reference data set, wherein the object of interest is an anatomy of interest and wherein the reference data set comprises at least one of computed tomography data, magnetic resonance data, ultrasound data, three-dimensional X-ray data, X-ray data or a model of the anatomy of interest to be imaged together with computed tomography specific information about an attenuation.

Therefore, the scan planning system may be adapted to use data acquired from other systems than the rotational X-ray C-arm examination apparatus in order to predict the field of view to be reconstructed and the image quality in the field of view.

According to another exemplary embodiment of the present invention, the scan parameter set is a three-dimensional scan parameter set. It should be noted, however, that the scan data set may have other dimensions, such as two dimensions or four dimensions (comprising time information).

Furthermore, the control unit may further be adapted to determine the optimal acquisition geometry corresponding to the anatomy of interest.

For example, the anatomy of interest may, according to a further exemplary embodiment of the invention, be defined by a user. For this purpose, the scan planning system may comprise an input unit adapted to receive an input from a user, which defines the anatomy of interest.

This defined anatomy of interest may be part of the scan parameter set on which basis the control unit predicts the field of view to be reconstructed and the image quality in the field of view.

The scan planning system may be adapted as a scan control unit that computes the optimal acquisition geometry with respect to a user-defined anatomy-of-interest.

According to another exemplary embodiment of the present invention, the control unit is further adapted to compute an optimal table position (or an optimal stand geometry, comprising, for example, source-image-distance, source-object-distance, C-arm trajectory, patient position) and an optimal detector format on the basis of the anatomy of interest indicated in the reference data set, resulting in computed data values, optimising a requested dose and a detector mode with respect to the previously acquired reference data set, resulting in optimised data values, outputting the computed and optimised data values, receiving, as user input, adapted data values, reconfiguring the scan planning system by changing the acquisition geometry automatically to the optimal settings, changing the detector mode and a requested dose level, and triggering a scan on the basis of at least one of the optimised data values, the computed data values, and the adapted data values.

Therefore, according to this exemplary embodiment of the present invention, a new scan set up is proposed and the user is guided, such that the acquisition settings are most favourable and the stand is positioned in an optimal and easy way. Furthermore, a check for collisions and conflicts is performed.

According to a further exemplary embodiment of the present invention, the scan planning system is adapted for performing a motion compensation on the basis of the reference data set. This may make the scan plan more robust.

According to a further exemplary embodiment of the present invention, a rotational X-ray C-arm examination apparatus for examination of an object of interest is provided, the examination apparatus comprising a scan planning system for planning a data acquisition process of the object of interest with the examination apparatus, the scan planning system comprising a control unit for predicting a field of view to be reconstructed and the image quality in the field of view on the basis of at least one of a scan parameter set and a previously acquired reference data set.

Furthermore, the examination apparatus may be configured as one of the group consisting of a material testing apparatus and a medical application apparatus.

A field of application of the invention may be medical imaging or material testing.

According to another exemplary embodiment of the present invention, a method of planning a data acquisition process of an object of interest with a rotational X-ray C-arm examination apparatus is provided, the method comprising the step of predicting a field of view to be reconstructed and the image quality in the field of view on the basis of at least one of a scan parameter set and a previously acquired reference data set.

Furthermore, the method may comprise the additional steps of computing an optimal stand position and an optimal detector format on the basis of the anatomy of interest indicated in the reference data set, resulting in computed data values, optimising a requested dose and a detector mode with respect to the previously acquired reference data set, resulting in optimised data values, outputting the computed and optimised data values, receiving adapted data values, which are being input by a user, reconfiguring the scan planning system by changing the stand geometry automatically to the optimal position, changing the detector mode and a requested dose level, and triggering a scan on the basis of at least one of the optimised data values, the computed data values, and the adapted data values.

This may provide for an automated method for planning a scan with a rotational X-ray imaging apparatus thereby reducing positioning effort and total X-ray dose.

According to another exemplary embodiment of the present invention, an image processing device for planning a data acquisition process of an object of interest with a rotational X-ray C-arm examination apparatus is provided, the image processing device comprising a memory for storing data set of the object of interest and a control unit adapted to carry out the above-mentioned method steps.

According to another exemplary embodiment of the present invention, a computer-readable medium may be provided, in which a computer program of planning a data acquisition process of an object of interest with a rotational X-ray C-arm examination apparatus is stored which, when being executed by a processor, causes the processor to carry out the above-mentioned method steps.

According to another exemplary embodiment of the present invention, a program element of examination of an object of interest may be provided, which, when being executed by a processor, causes the processor to carry out the above-mentioned method steps.

The planning process may be embodied as the computer program, i.e. by software, or may be embodied using one or more special electronic optimisation circuits, i.e. in hardware, or the method may be embodied in hybrid form, i.e. by means of software components and hardware components.

The program element according to an exemplary embodiment of the invention is preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the World Wide Web, from which it may be downloaded into image processing units or processors, or any suitable computers.

It may be seen as the gist of an exemplary embodiment of the present invention that a scan planning system is provided which is capable of predicting the reconstructed field of view (FOV) as well as the image quality of the field of view with respect to the actual three-dimensional scan parameter set and previously acquired images or information, which may have been acquired from other modalities. Furthermore, the scan planning system may be accomplished by a stand control unit that computes the optimal acquisition geometry with respect to a user-defined anatomy of interest.

Specific to scan planning for rotational X-ray compared to known methods for diagnostic devices is the (possible) use of pre-interventional data from other modalities, registration means to relate the respective (volumetric) data to actual fluoroscopic data and the indication of the expected image quality resulting from the actual scan parameter set (the limited field of view may be one reason for the limited image quality).

According to one aspect of the present invention, the three-dimensional X-ray scan planning system may ease existing three-dimensional functionalities and may be capable of reducing the total X-ray dose and may be integrated in current C-arm based systems with little additional efforts.

These and other aspects of the present invention will become apparent from and elucidated with reference to the embodiments described hereinafter.

The invention will now be described, by way of example only, with reference to the accompanying drawings, in which.

The illustrations are schematic. In different drawings, similar or identical elements are provided with the same reference numerals.

Figure 1:
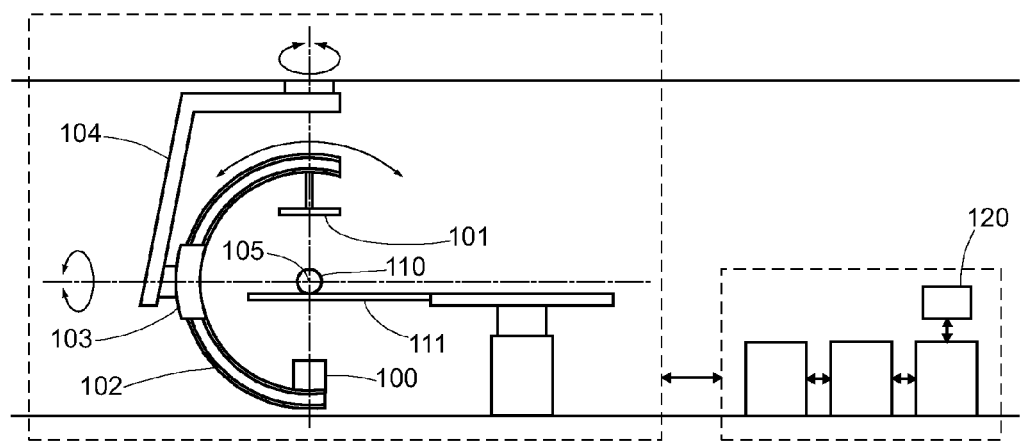
FIG. 1 shows a schematic representation of an exemplary embodiment of the present invention adapted as a X-ray C-arm examination apparatus.

FIG. 1 shows a schematic drawing of an exemplary embodiment of the present invention adapted to a X-ray C-arm examination apparatus. An X-ray source 100 and a flat detector 101 with a large sensitive area are mounted to the ends of a C-arm 102. The C-arm 102 is held by curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are effected by servo motors. The axes of the three rotational movements and the cone-beam axis always meet in a single fixed point, the "isocenter" 105 of the X-ray examination apparatus. There is a certain volume around the isocenter that is projected by all cone beams along the source trajectory. The shape and size of this "volume of projection" (VOP) depend on the shape and size of the detector and on the source trajectory. In FIG. 1, the ball 110 indicates the biggest isocentric ball that fits into the VOP. The object (e.g. a patient or an item of baggage) to be imaged is placed on the table 111 such that the object's volume of interest (VOI) fills the VOP. If the object is small enough, it will fit completely into the VOP; otherwise, not. The VOP therefore limits the size of the VOI.

The various rotational movements are controlled by a control unit 120. Each triple of C-arm angle, sleeve angle, and L-arm angle defines a position of the X-ray source. By varying these angles with time, the source can be made to move along a prescribed source trajectory. The detector at the other end of the C-arm makes a corresponding movement. The source trajectory will be confined to the surface of an isocentric sphere.

3D X-ray imaging gains popularity and its clinical application fields are broadened. While for neuro applications the scan field is often well defined, three-dimensional imaging especially in the thorax or in the abdomen may be more difficult due to a more compound anatomy and patient motion.

Prior to the rotational acquisition the user has to position the anatomy-of-interest manually in the isocentre of the system. Thereby the source-image and the source-isocentre distance are fixed in current system to ease the calibration effort. However, the table position can be varied in height and lateral position under occasionally intensive fluoroscopic control. Moreover the C-arm has to be moved from the end position to the start position of the scan trajectory assuring that collisions with patient and medical equipment are avoided. Start and end position may be user-defined, however, it is advised to use only protocol-defined positions. During these steps it is essential to include the three-dimensional anatomy-of-interest into the field-of-view of the subsequent reconstruction and to ensure best possible image quality for the scanned volume avoiding truncations. Further parameters, which influence diagnostic scan quality as well, have to be considered. These are Scan mode (roll scan or propeller scan)
Type and position of filter (wedges, shutter, bowtie filter)
Detector format, detector orientation (landscape or portrait) and detector sensitivity (gain mode and dynamic range of acquisition) (i.e. the detector mode)
Dose request (influencing total applied X-ray dose)
X-ray spectrum, kV-settings
CA injection parameters In clinical practice it is often difficult to outbalance clinical and technical requirements potentially resulting in low quality reconstructions and the necessity to perform additional rotational acquisitions. Dedicated rotational scan planning software may improve ease of use of current X-ray systems reducing positioning effort and total X-ray dose.

According to an aspect of the present invention, a system and method to improve 3D scan setup are provided. The main feature consists of a software package that is capable of predicting the reconstructed field-of-view as well as the image quality in the field-of-view with respect to the actual 3D scan parameter set and previously acquired images/information (possibly from other modalities). Another essential feature is a stand control unit that computes the optimal acquisition geometry with respect to the user-defined anatomy of interest. Specific to scan planning for rotational X-ray compared to known methods for diagnostic devices is the (possible) use of pre-interventional data from other modalities,
the use of registration techniques to relate respective data to actual fluoroscopy data and
the indication of the image quality resulting from the limited field-of-view of rotational X-ray acquisitions.

Figure 3:
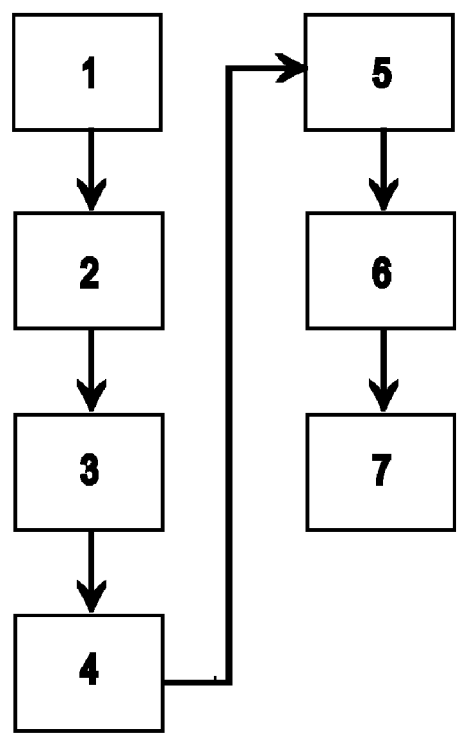
FIG. 3 shows a flow-chart of an exemplary method according to the present invention.

FIG. 3 shows a flow-chart of a method according to an exemplary embodiment of the present invention, the method comprising the following steps:

Step 1: Read and visualise 3D reference data (pre-interventional or interventional CT imaging, magnetic resonance imaging, ultra sound imaging, 3D rotational X-ray imaging, or X-ray imaging; possibly also a model of the anatomy with CT specific information about attenuation); in case that there is no volume available read and visualise biplane or pseudo biplane fluoroscopies of the treatment side.

Step 2: Align the reference data to the rotational acquisition geometry of interest. The rotational acquisition geometry of interest may be represented by three different data sets, namely to a pre-defined scan parameter set, to the actual stand geometry, and to the acquisition geometry of pre-selected data sets. The different imaging coordinate systems are aligned to each other using well-known registration methods. To make the registration task more robust fluoroscopic images may be acquired to update the patient position with respect to acquisition geometry of the reference data set. Prominent feature (like ribs, bones, vertebras) are extracted from the available images and may be used to refine registration.

Then, in step 3, further system parameters relevant for 3D rotational imaging are specified by the user or read out from system memory to complete/update the scan parameter set. Such system parameters may comprise the scan mode (such as propeller scan or roll scan), the stand geometry (such as angulation, table position), the scan trajectory given by start and end position of the C-arm, the detector format, detector orientation (e.g. landscape or portrait) and detector sensitivity (such as gain mode and dynamic range of acquisition), the dose request and voltage-settings, and the type and position of a filter (such as wedges, shutter, bowtie filter). Then, in step 4, a virtual C-arm rotation is computed according to the actual scan setup.

In step 5, the field-of-view and isocentre of the given scan setup is visualised in the reference data set and/or with respect to the actual fluoroscopic images, the regions that may be seriously affected by artefacts like (geometrical and patient-specific) truncations or clipping are highlighted.

Figure 2:
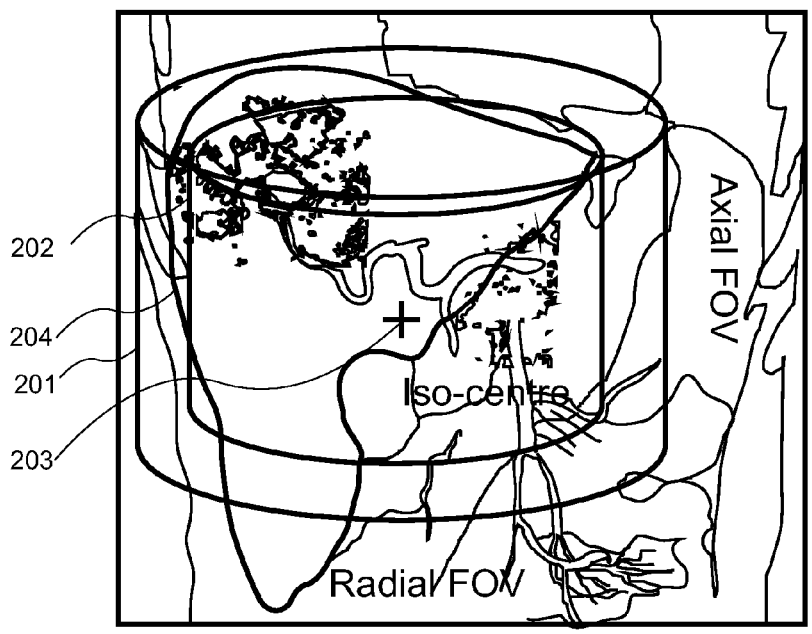
FIG. 2 shows a schematic representation of a liver scan plan, visualisation of actual iso-centre, total field of view and best quality field of view in three dimensions.

Such a scan plan 200 of a liver 204 according to an exemplary embodiment of the present invention is depicted in FIG. 2. With respect to a reference image the main features of the scan setup are highlighted. Reference numeral 201 depicts the contour of the reconstructable field-of-view (it should be noted that the cylinder shape may only be valid for an ideal parallel projection geometry; using cone beam the cylinder is covered to both sides with a "Chinese" hat). The cylinder 202 outlines the volume of best image quality. The cross 203 points to the isocentre of the scan.

Step 6: Allow the user to move the isocentre and to define the anatomy-of-interest in the scan plan. In case that there is no volume available to do the planning, it should be possible that the user indicates the region-of-interest on the (frontal and lateral) fluoroscopic images.

Step 7: Propose new scan set-up and guide the user, such that the acquisition settings are most favourable and the stand is positioned in an optimal and easy way. Check for collisions and conflicts. Step 7 may comprise:

Computing of the optimal acquisition geometry and the minimal required detector format on base of the VOI indicated in the reference data, optimising the requested dose as well as the detector mode (gain) with respect to previously acquired volume data, presenting the user the calculated values and allowing him to adapt them, reconfiguring the system by moving the table automatically to the optimal position and changing gain mode and the requested dose level. Then, the scan is performed.

Figure 4:
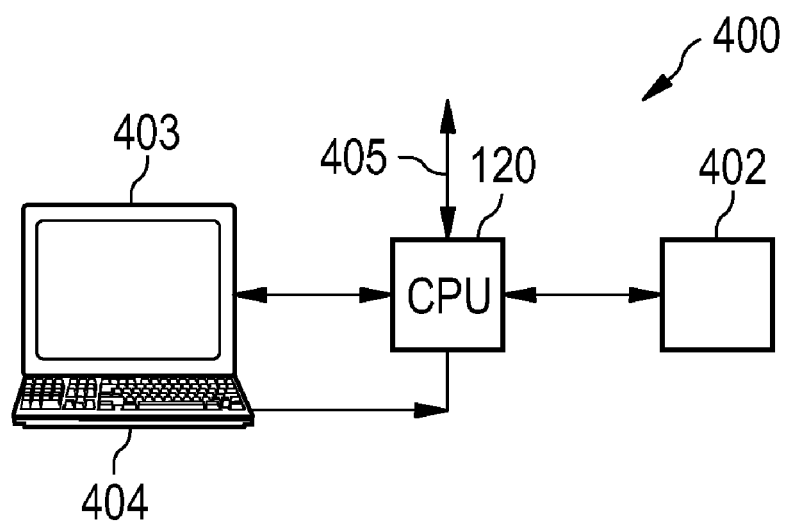
FIG. 4 shows an exemplary embodiment of an image processing device according to the present invention, for executing an exemplary embodiment of a method in accordance with the present invention.

FIG. 4 depicts an exemplary embodiment of a data processing device 400 according to the present invention for executing an exemplary embodiment of a method in accordance with the present invention. The data processing device 400 depicted in FIG. 4 comprises a central processing unit (CPU) or image processor 120 connected to a memory 402 for storing an image depicting an object of interest, such as a patient or an item of baggage. The data processor 401 may be connected to a plurality of input/output network or imaging devices, such as a rotational C-arm examination apparatus. The data processor 120 may furthermore be connected to a display device 403, for example, a computer monitor, for displaying information or an image computed or adapted in the data processor 120. An operator or user may interact with the data processor 120 via a keyboard 404 and/or other output devices, which are not depicted in FIG. 4.

Furthermore, via the bus system 405, it may also be possible to connect the image processing and control processor 120 to, for example, a motion monitor, which monitors a motion of the object of interest. In case, for example, a lung of a patient is imaged, the motion sensor may be an exhalation sensor. In case the heart is imaged, the motion sensor may be an electrocardiogram. Thus, the patient may no longer be required to hold his breath during the rotational acquisition. In any case, such a motion detection/compensation may make the scan plan more robust. It should be noted that motion may be detected via respective sensors as described above or extracted out of the (four dimensional, i.e. time information comprising) reference data.

A field of application of the invention may be any kind of X-ray guided interventions making use of 3D acquisition protocols. The new scan planning feature according to an aspect of the invention may supplement existing 3D functionality and may be integrated in current C-arm based systems with low additional effort.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A scan planning system for planning a data acquisition process of an object of interest with a rotational X-ray C-arm examination apparatus, the scan planning system comprising:
   a control unit for predicting image content of a three-dimensional field of view to be reconstructed and an image quality of the image content in the three-dimensional field of view on the basis of a three-dimensional scan parameter set and a previously acquired reference data set.

2. The scan planning system of claim 1, wherein:
   the reference data set is a three dimensional reference data set;
   the object of interest is an anatomy of interest; and
   the reference data set comprises at least one of computed tomography data, magnetic resonance data, ultra sound data, three-dimensional X-ray data, X-ray data, and a model of the anatomy of interest to be imaged together with computed tomography specific information about an attenuation.

3. The scan planning system of claim 1, wherein the control unit is further adapted to determine an acquisition geometry and acquisition settings corresponding to an anatomy of interest.

4. The scan planning system of claim 3, further comprising:
   an input unit adapted to receive an input from a user;
   wherein the input defines the anatomy of interest.

5. The scan planning system of claim 3, wherein the control unit is further adapted to:
   optimize a requested dose with respect to the previously acquired reference data set, resulting in optimized data values; and
   output the optimized data values.

6. The scan planning system of claim 1, further adapted for performing a motion compensation on the basis of the reference data set.

7. A rotational X-ray C-arm examination apparatus for examination of an object of interest, the examination apparatus comprising:
   a scan planning system for planning a three-dimensional rotational data acquisition process of the object of interest with the rotational X-ray C-arm examination apparatus, the scan planning system comprising:
   a control unit for predicting image content of a three-dimensional field of view to be reconstructed and an image quality of the image content in the three-dimensional field of view on the basis of a three-dimensional scan parameter set and a previously acquired reference data set.

8. The examination apparatus of claim 7, configured as one of the group consisting of a material testing apparatus and a medical application apparatus.

9. A method of planning a data acquisition process of an object of interest with a rotational X-ray C-arm examination apparatus, the method comprising the step of:
   predicting image content of a three-dimensional field of view to be reconstructed and an image quality of the image content in the three-dimensional field of view on the basis of a three-dimensional scan parameter set and a previously acquired reference data set;
   wherein the predicting is performed by a data processing device.

10. The method of claim 9, further comprising the steps of:
    optimizing a requested dose with respect to the previously acquired reference data set, resulting in optimized data values; and
    outputting the optimized data values.

11. An image processing device for planning a data acquisition process of an object of interest with a rotational X-ray C-arm examination apparatus, the image processing device comprising:
    a memory for storing a data set comprising data of an object of interest; and
    a control unit for predicting image content of a three-dimensional field of view to be reconstructed and an image quality of the image content in the three-dimensional field of view on the basis of a scan parameter set and a previously acquired reference data set.

12. A computer-readable medium, in which a computer program of planning a data acquisition process of an object of interest with a rotational X-ray C-arm examination apparatus is stored which, when being executed by a processor, causes the processor to carry out the step of:
    predicting image content of a three-dimensional field of view to be reconstructed and an image quality of the image content in the three-dimensional field of view on the basis of a three-dimensional scan parameter set and a previously acquired reference data set.

13. An apparatus comprising:
    a processor configured to:
    predict image content of a three-dimensional field of view to be reconstructed on the basis of a previously acquired reference data set and a scan parameter set for three-dimensional imaging using a rotational X-ray examination apparatus including an opposed X-ray source and detector disposed on a support providing rotation of the X-ray source around at least one axis.

14. The apparatus of claim 13, wherein the processor is further configured to visualize the predicted image content and an isocenter of the three-dimensional field of view to be reconstructed.

15. The apparatus of claim 13, wherein the scan parameter set includes an isocenter of the three-dimensional field of view and the processor is further configured to receive an updated isocenter and to predict updated image content of the three-dimensional field of view to be reconstructed.

16. The apparatus of claim 13, wherein the processor is further configured to receive an identification of anatomy of interest in the predicted image content of a three-dimensional field of view to be reconstructed and to optimize at least one of radiation dose, detector mode, and the scan parameter set respective to the identified anatomy of interest.

17. The apparatus of claim 13, wherein the scan parameter set includes at least one of (1) scan mode selected from a group consisting of propeller scan mode and roll scan mode and (2) scan trajectory.

18. The apparatus of claim 13, wherein the processor is further configured to predict a volume of best image quality within the three-dimensional field of view.

19. The apparatus of claim 13, further comprising:
said rotational X-ray examination apparatus including said opposed X-ray source and detector disposed on said support providing rotation of the X-ray source around at least one axis; and
a control unit configured to control the rotational X-ray examination apparatus to perform three-dimensional imaging including moving the X-ray source along a prescribed source trajectory in accordance with the scan parameter set.

* * * * *